(12) United States Patent
Urushiya et al.

(10) Patent No.: US 8,842,807 B2
(45) Date of Patent: Sep. 23, 2014

(54) X-RAY MOVING IMAGE RADIOGRAPHING APPARATUS

(75) Inventors: Hiroyuki Urushiya, Saitama (JP); Osamu Tsujii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/542,394

(22) Filed: Jul. 5, 2012

(65) Prior Publication Data

US 2012/0277581 A1    Nov. 1, 2012

Related U.S. Application Data

(63) Continuation of application No. 12/421,120, filed on Apr. 9, 2009, now Pat. No. 8,249,216.

(30) Foreign Application Priority Data

Apr. 14, 2008   (JP) .................................. 2008-104300

(51) Int. Cl.
*A61B 6/02* (2006.01)
*A61B 6/00* (2006.01)
*A61B 6/12* (2006.01)

(52) U.S. Cl.
CPC ................. *A61B 6/504* (2013.01); *A61B 6/547* (2013.01); *A61B 6/5247* (2013.01); *A61B 6/4417* (2013.01); *A61B 6/5217* (2013.01); *A61B 6/12* (2013.01); *A61B 6/405* (2013.01); *A61B 6/4441* (2013.01); *A61B 6/463* (2013.01); *A61B 6/481* (2013.01); *A61B 6/482* (2013.01); *A61B 6/4028* (2013.01); *A61B 6/4291* (2013.01)
USPC ........................................................... 378/63

(58) Field of Classification Search
CPC .. A61B 6/4417; A61B 6/5217; A61B 6/5247; A61B 6/547
USPC ........................................................... 378/63
See application file for complete search history.

(56) References Cited

U.S. PATENT DOCUMENTS

| 5,490,197 | A | * | 2/1996 | Albert et al. ................... 378/113 |
| 5,859,893 | A | * | 1/1999 | Moorman et al. ............ 378/154 |
| 6,292,531 | B1 | * | 9/2001 | Hsieh ................................ 378/37 |
| 6,368,269 | B1 | * | 4/2002 | Lane .............................. 600/126 |
| 7,724,875 | B2 | * | 5/2010 | Jabri et al. .................... 378/98.9 |

(Continued)

FOREIGN PATENT DOCUMENTS

| JP | H04-013381 A | 1/1992 |
| JP | 05161635 A | 6/1993 |

(Continued)

*Primary Examiner* — Thomas R Artman
(74) *Attorney, Agent, or Firm* — Canon USA, Inc. IP Division (57) ABSTRACT

An X-ray moving image radiographing apparatus includes an X-ray detector configured to detect an X-ray transmitting through a subject to acquire a subject image, an image processing unit configured to process an X-ray radiographic image output from the X-ray detector, and a control unit configured to capture a mask image by selectively scanning X-ray focal positions of an X-ray source which has a plurality of X-ray focal points so that an X-ray incident angle varies with respect to a target point of the subject, and to capture a moving image after a predetermined work is performed on the subject by selectively scanning X-ray focal positions of the X-ray source similar to the scanning operation used to capture the mask image.

16 Claims, 6 Drawing Sheets

(56) References Cited

U.S. PATENT DOCUMENTS

| | | | |
|---|---|---|---|
| 7,835,785 B2* | 11/2010 | Scully et al. | 600/424 |
| 7,889,227 B2* | 2/2011 | Rahn et al. | 348/65 |
| 7,949,089 B2* | 5/2011 | Dafni et al. | 378/9 |
| 8,364,242 B2* | 1/2013 | Li | 600/424 |
| 2004/0199067 A1* | 10/2004 | Bock et al. | 600/411 |
| 2007/0061726 A1* | 3/2007 | Rahn et al. | 715/719 |
| 2007/0078334 A1* | 4/2007 | Scully et al. | 600/424 |
| 2008/0281189 A1* | 11/2008 | Komuro et al. | 600/424 |
| 2008/0283771 A1* | 11/2008 | Li | 250/459.1 |
| 2009/0281383 A1* | 11/2009 | Papineni et al. | 600/109 |
| 2011/0016430 A1* | 1/2011 | Fram et al. | 715/838 |
| 2012/0294498 A1* | 11/2012 | Popovic | 382/128 |

FOREIGN PATENT DOCUMENTS

| | | |
|---|---|---|
| JP | H06-070237 A | 3/1994 |
| JP | 11113892 | 4/1999 |
| JP | 2005261838 A | 9/2005 |

* cited by examiner

X-RAY MOVING IMAGE RADIOGRAPHING APPARATUS

CROSS-REFERENCE TO RELATED APPLICATIONS

This application is a Continuation of prior U.S. patent application Ser. No. 12/421,120 filed Apr. 9, 2009, which claims the benefit of Japanese Patent Application No. 2008-104300, filed Apr. 14, 2008. The disclosures of the above-named applications are hereby incorporated by reference herein in their entirety.

BACKGROUND OF THE INVENTION

1. Field of the Invention

The present invention relates to an X-ray moving image radiographing apparatus that captures X-ray radiographic images while a medical professional is providing treatment with respect to a subject.

2. Description of the Related Art

Recently, a technique of Digital Subtraction Angiography (DSA) imaging has become widely used in angiography imaging. DSA imaging is an X-ray radiographing method wherein an X-ray radiographic image is captured before injection of a contrast medium to form a mask image. An X-ray radiographic image is captured after injecting the contrast medium into a blood vessel of a subject, and a background is removed by subtracting the mask image from the contrast medium-injected X-ray radiographic image. Thus, an image of blood vessels to which the contrast medium was injected can be displayed.

An important aspect of DSA imaging is to comprehend a running state of blood vessels. The blood vessels within a human body reside in a three-dimensional space. However, when the blood vessels are subjected to the X-ray radioscopic imaging, information about the blood vessels is compressed into two-dimensional information from three-dimensional information. Consequently, it is difficult to accurately comprehend a running state of the complicated blood vessels by observing a simpler two-dimensional image.

To comprehend the running state of the blood vessel in a three-dimensional manner, a technique of rotation DSA imaging is developed. In rotation DSA imaging, an X-ray radiographic image is captured by an X-ray radiographing apparatus having an X-ray detector. The X-ray detector includes, for example, a C-shaped arm that has an X-ray source disposed on one end and an image intensifier or a flat panel detector (FPD) on the other end. The X-ray radiographing apparatus captures X-ray radiographic images by rotating the C-shaped arm around the subject, to form mask images for every one of rotation angles. After injecting a contrast medium into a blood vessel of the subject, the X-ray radiographing apparatus captures further X-ray radiographic images at the same rotational angles as those used in forming the mask images. Finally, the X-ray radiographing apparatus subtracts the mask images from the X-ray radiographic images of the corresponding rotational angles captured after injection of the contrast medium. Accordingly, moving images of only the blood vessels specified by the contrast medium can be displayed.

Further, in the angiography imaging, when the contrast medium is injected into the blood vessel of the subject, the contrast medium spreads over a wide area at high speed, so that relatively large X-ray detector is required in order to completely capture images of the spreading condition of the contrast medium. Also, it is required to continuously irradiate an X-ray over the entire area where the contrast medium is spreading.

Furthermore, for X-ray radioscopic imaging performed by a catheter or an endoscope, it is may be required to capture images to irradiate the X-ray over a wider area than an area where the catheter or the endoscope is operated.

In addition to the above described X-ray radiographic imaging method, Japanese Patent Application Laid-Open No. 06-217964 discusses a technique relating to an X-ray radiographing apparatus that electronically performs raster scanning in order to detect a focal position of the X-ray.

However, in the rotation DSA imaging, the C-shaped arm needs to be rotated at each time the mask images are captured and the angiography imaging is performed. Since the C-shaped arm is mechanically rotated, an operator must rotate the C-shaped arm with precision. More specifically, the operator needs to pay attention to the C-shaped arm to prevent the arm from striking a table or anything around the C-shaped arm, which may further complicate capturing images. Further, in the angiography imaging, the X-ray is continuously irradiated onto the entire area where the contrast medium is spreading after the injection of the contrast medium, so that X-ray irradiation dosage of the subject is extremely large as well as that of the operator who captures the images. Also, in the X-ray radioscopic imaging using the catheter or the endoscope, the X-ray irradiation dosage of the subject and the operator is extremely large.

SUMMARY OF THE INVENTION

According to an aspect of the present invention, an X-ray moving image radiographing apparatus includes an X-ray detector configured to detect an X-ray transmitting through a subject to acquire a subject image, an image processing unit configured to process an X-ray radiographic image output from the X-ray detector, and a control unit configured to capture a mask image by selectively scanning X-ray focal positions of an X-ray source which has a plurality of X-ray focal points so that an X-ray incident angle varies with respect to a target point of the subject, and to capture a moving image after a predetermined work is performed on the subject by selectively scanning X-ray focal positions of the X-ray source similar to the scanning operation used to capture the mask image.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will be described in detail below with reference to the drawings.

Figure 1:
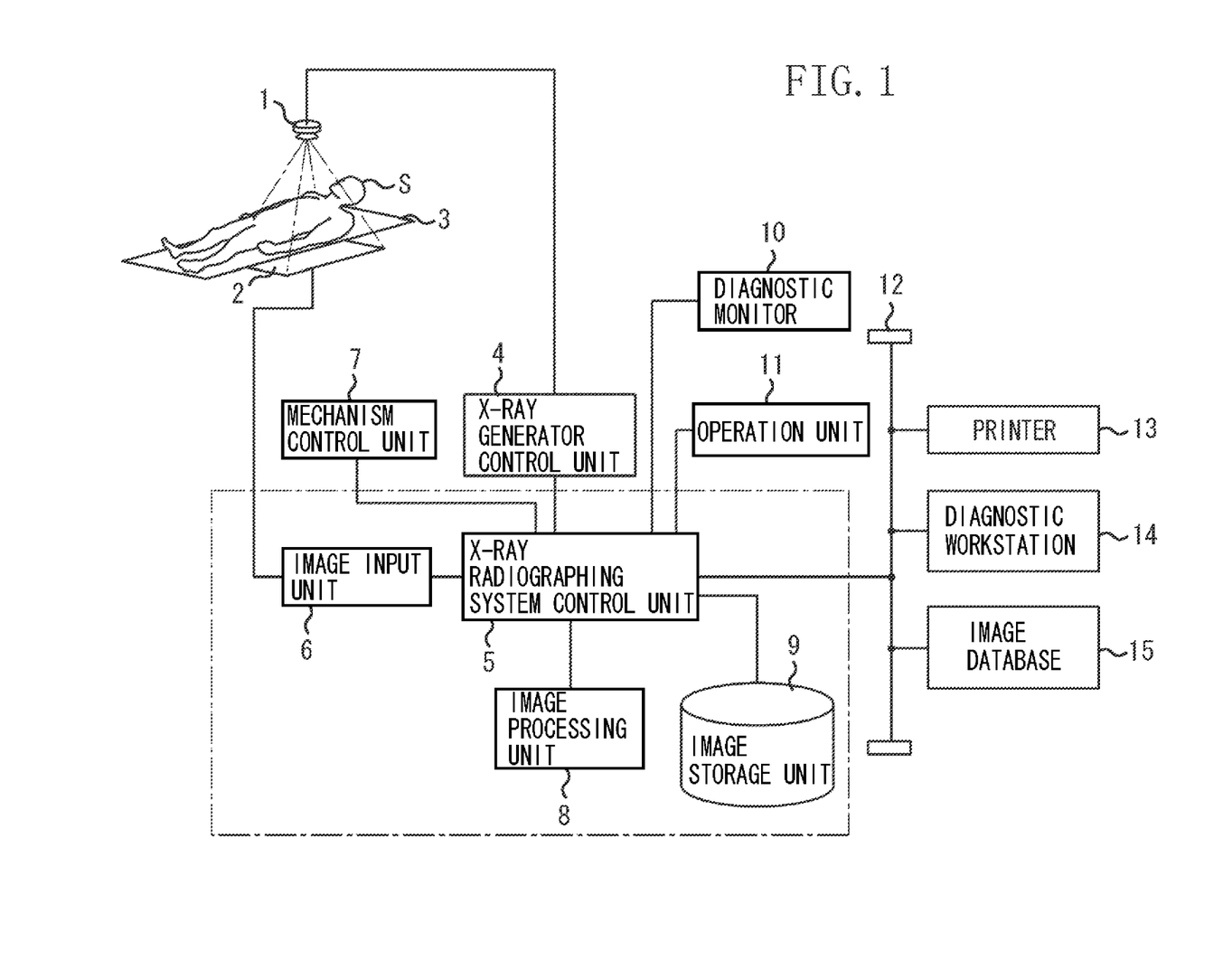
FIG. 1 is a block diagram illustrating an X-ray moving image radiographing system according to an exemplary embodiment of the present invention.

FIG. 1 is a block diagram illustrating an example of an X-ray moving image radiographing system according to an exemplary embodiment of the present invention. In the X-ray moving image radiographing system, an X-ray source 1 which generates an X-ray and an X-ray detector 2 which detects the X-ray generated from the X-ray source 1 are arranged to face each other. Further, a table 3 on which a subject S lies down is arranged between the X-ray source 1 and the X-ray detector 2. As described below, the X-ray source 1 is provided with a lead diaphragm 1a, and the X-ray detector 2 is provided with a grid 2a.

The X-ray source 1 is connected to an output of an X-ray radiographing system control unit 5 via an X-ray generator unit control unit 4 which controls generation of an X-ray. An output of the X-ray detector 2 is connected to the X-ray radiographing system control unit 5 via an image input unit 6. The X-ray radiographing system control unit 5 is connected to a mechanism control unit 7 which controls a mechanism of the system, an image processing unit 8 which processes images, an image storage unit 9 which stores images, a diagnostic monitor 10 which displays images, and an operation unit 11 which performs various operations. Further, the X-ray radiographing system control unit 5 is connected to an external printer 13, a diagnostic workstation 14, and an image database 15 via a network 12.

The X-ray generated from the X-ray source 1 which is controlled by the X-ray generator unit control unit 4, transmits through the subject S and is detected by the X-ray detector 2 as a subject image. The detected X-ray radiographic image is input into the X-ray radiographing system control unit 5 as image data via the image input unit 6. The image data is subjected to image processing such as correction of the X-ray detector 2, preprocessing including log conversion, noise removal, sharpening, and image quality enhancement processing such as dynamic range compression, and an image analysis in the image processing unit 8.

The image having been subjected to image processing is displayed on the diagnostic monitor 10. For the moving image radiography, the image processing is continuously repeated to capture images in chronological order and the captured images are continuously displayed on the diagnostic monitor 10. Further, the images captured in chronological order are stored in the image storage unit 9, or output to the printer 13, the diagnostic workstation 14, and the image database 15 via the network 12.

Figure 2:
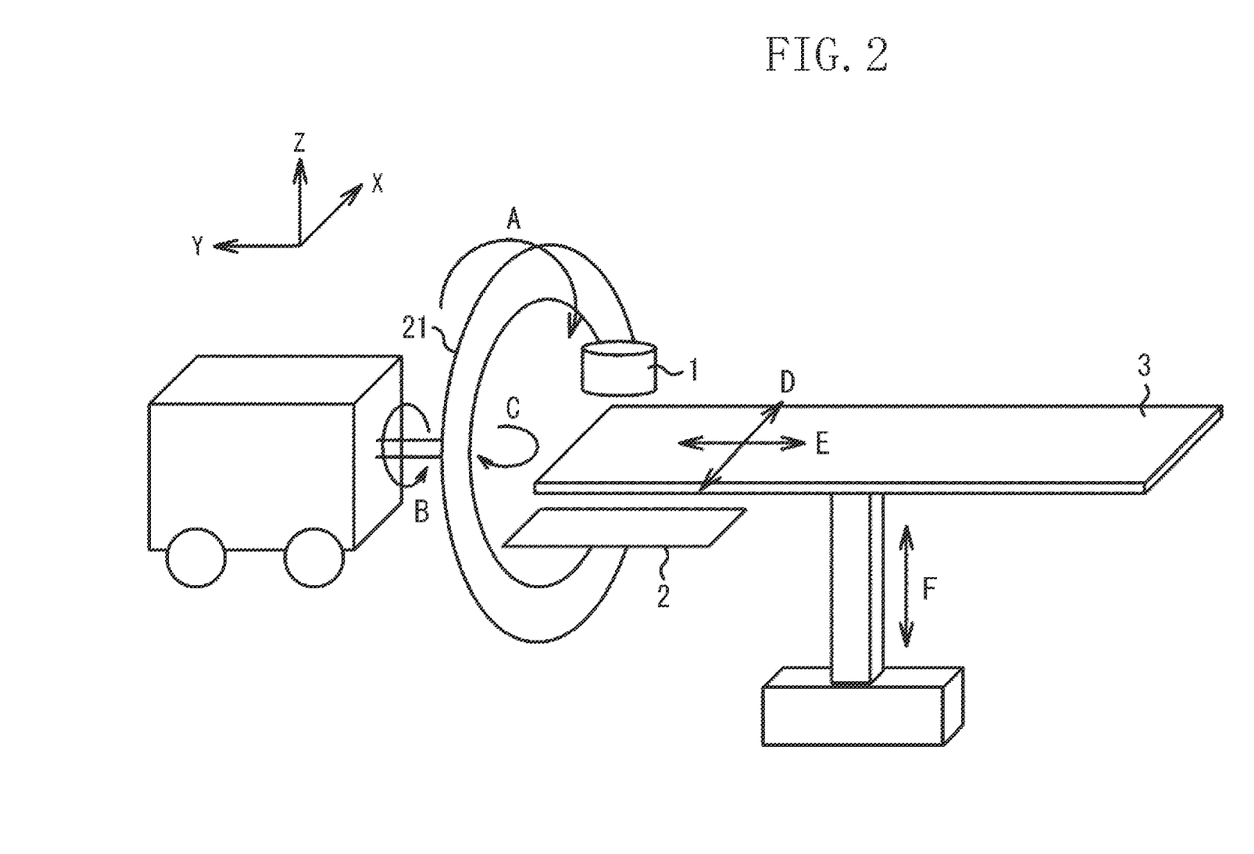
FIG. 2 is a configuration diagram of a C-shaped arm.

FIG. 2 is a configuration diagram of a C-shaped arm, as a retaining mechanism to retain the X-ray source 1 and the X-ray detector 2. On both ends of the C-shaped arm 21, the X-ray source 1 and the X-ray detector 2 are fixed. The C-shaped arm 21 can rotate in three directions, i.e., directions of X axis, Y axis, and Z axis which are indicated by arrows A, B, and C. The table 3 can also move interlockingly with the C-shaped arm 21 in three directions, i.e., directions of front-to-rear, right-to-left, and up-and-down which are indicated by arrows D, E, and F.

The table 3 and the C-shaped arm 21 are controlled by the mechanism control unit 7 to capture images of the subject S in any directions and at any positions, which is not illustrated in FIG. 2.

Figure 3A:
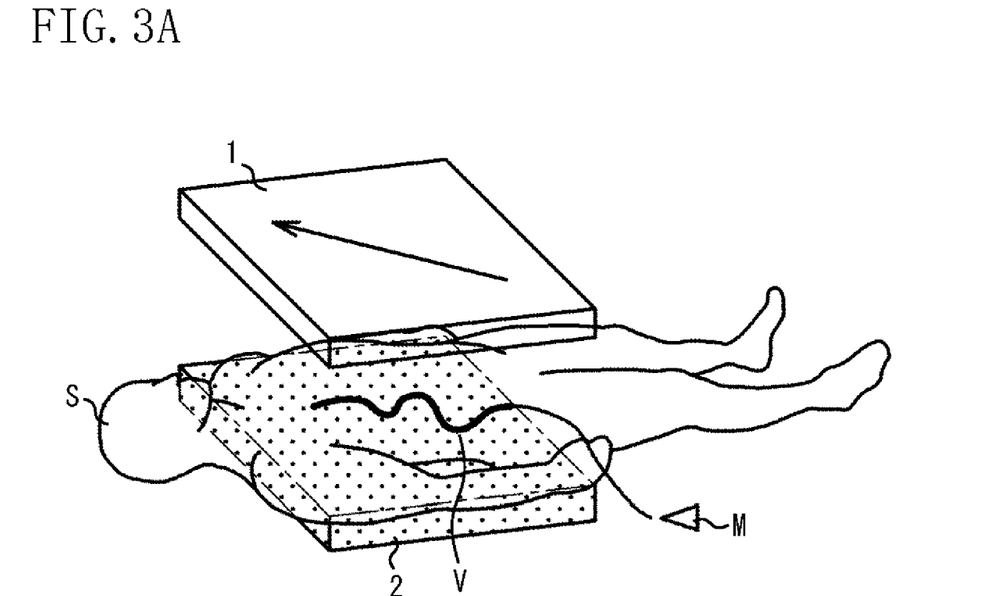
FIGS. 3A and 3B illustrate how to capture images according to angiography imaging.
Figure 3B:
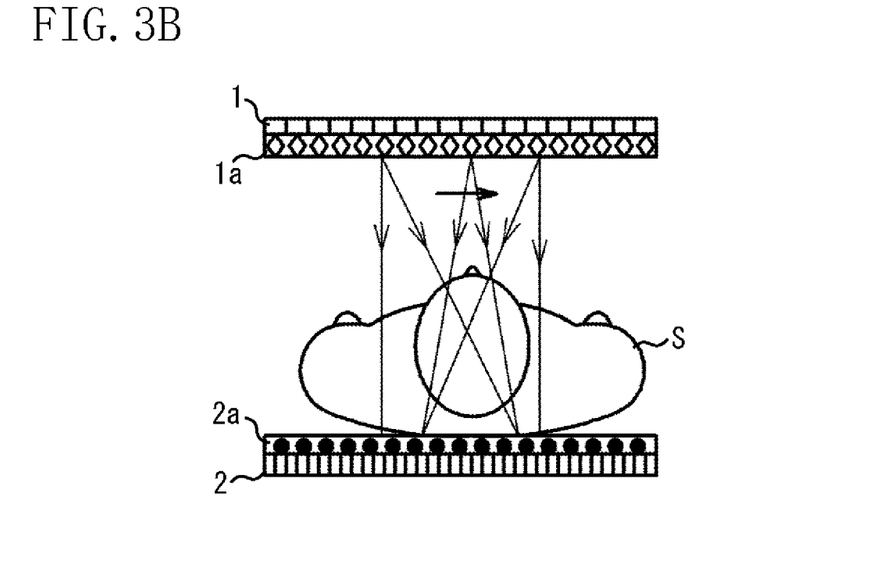

By using the above described X-ray moving image radiographing system, the rotation DSA imaging and the X-ray radioscopic imaging using the catheter or the endoscope are performed. In the rotation DSA imaging, the mask images are captured before injecting a contrast medium. Conventionally, the images are captured while the C-shaped arm 21 is rotated in an A direction or a B direction as illustrated in FIG. 2. However, according to the present exemplary embodiment, once the C-shaped arm 21 is moved and positioned at the beginning, X-ray focal positions are scanned in an area where the contrast medium is expected to spread over in a predetermined direction, as illustrated in FIG. 3A, without driving the C-shaped arm 21 during the image capturing process. FIG. 3B is a cross sectional view of the above processing from a head of the subject S.

In the X-ray source 1, the X-ray focal points of a number of N×M are arranged on a plane surface which is sectioned by the lead diaphragm 1a. By selectively scanning these X-ray focal points in the above described direction, an X-ray irradiation result similar to that of the X-ray irradiation with driving the C-shaped arm 21 can be obtained. The image of every X-ray focal position can be captured by using the X-ray detector 2 having a grid 2a during a scanning operation of the X-ray focal positions. The captured images are referred to as mask images.

After capturing the mask images, a contrast medium M is injected into a blood vessel V of the subject S. When the contrast medium M circulates around the blood vessel V, the X-ray focal positions are scanned to capture images according to a method as in the case of forming the mask images. At the time, the prior mask images are respectively accorded with the corresponding images which were captured at the same X-ray focal positions, and are subtracted therefrom to remove unnecessary background. Accordingly, a moving image of only the blood vessel V specified with the contrast medium M can be obtained. Further, since the X-ray focal positions change, the blood vessel V specified with the contrast medium M can be observed from a variety of X-ray incident angles by continuously displaying the subtracted images as the X-ray focal positions are scanned. Accordingly, a running state of the complicated bloods vessels V, a lump and constriction on the blood vessels V, or the like, can be accurately comprehended in three dimensions. Energy of X-ray to be irradiated for capturing the mask images may be different from energy of X-ray to be irradiated for capturing images after the contrast medium M is injected into the blood vessel V. The X-ray moving image radiographing apparatus can capture images through DSA imaging without involving any mechanical actions after being positioned at the beginning. To assist scanning of the X-ray focal points, the C-shaped arm 21 may also be optionally moved.

Figure 4A:
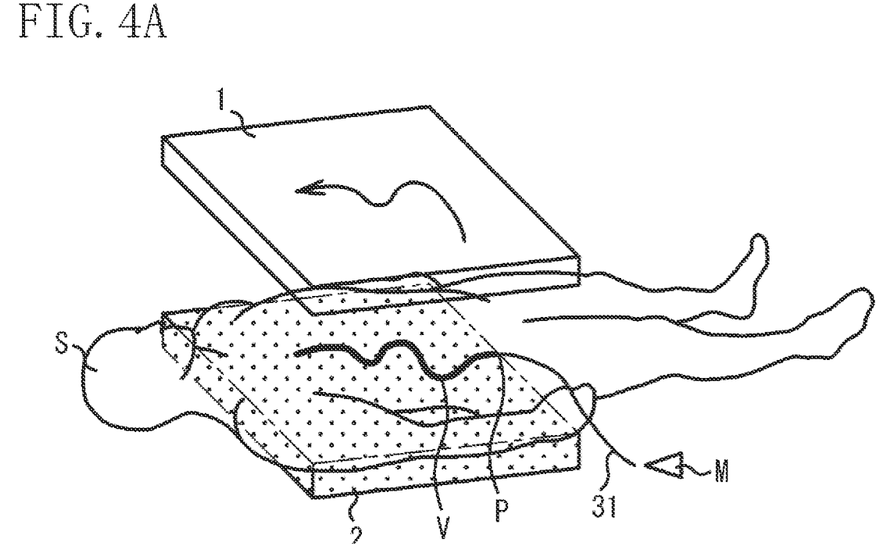
FIGS. 4A and 4B illustrate how to capture images according to catheter imaging.
Figure 4B:
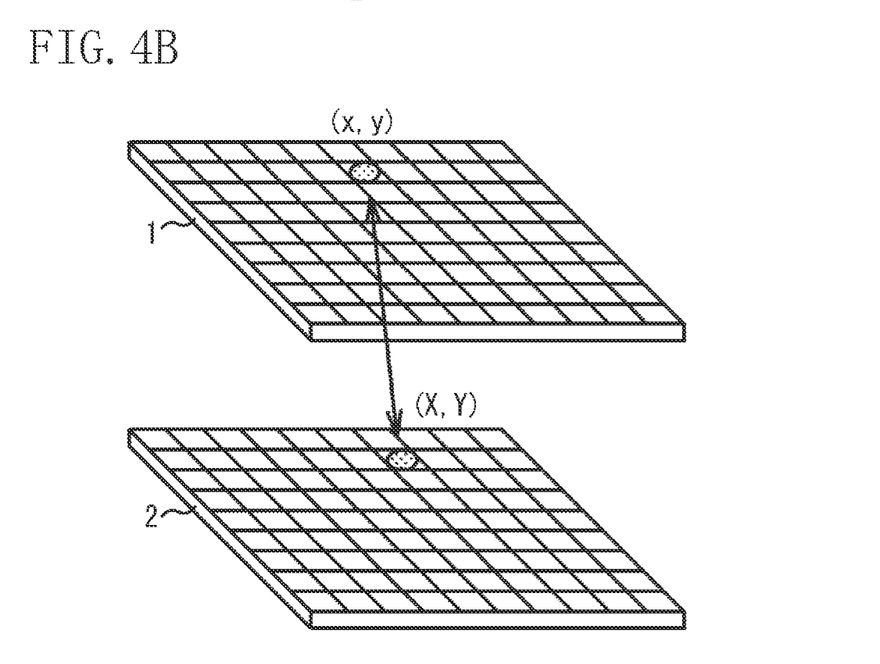

In a second exemplary embodiment, the X-ray radioscopic imaging is performed by using the catheter or the endoscope. FIG. 4A illustrates how to capture images by using the catheter. In FIG. 4A, a catheter 31 is initially inserted into the blood vessel V of the subject S to get the catheter 31 to reach a target position P. At the time, the X-ray focal positions are selected to move so as to trace a top end of the catheter 31. As illustrated in FIG. 4B, the X-ray source 1 and the X-ray detector 2 are arranged to face each other and each of the X-ray focal positions of the X-ray source 1 is given a coordinate of (x, y) and each of pixel positions of the X-ray detector 2 is given a coordinate of (X, Y). Correspondence relationships between the coordinates (X, Y) and the coordinates (x, y) which are spatially closest to each other are made into a table.

Accordingly, a position of the top end of the catheter 31 is determined from an X-ray radiographic image. In order to determine the position of the top end of the catheter 31, the immediately preceding image is subtracted from each of the images in chronological order, and a portion where the top end of the catheter 31 moves is extracted to find a coordinate of the portion.

When the coordinate of the position of the top end of the catheter 31, namely a positional coordinate in the X-ray detector 2 is determined, a coordinate of the X-ray focal position of the X-ray source 1 corresponding to the position of the top end of the catheter 31 can be acquired from the above described table of correspondence relationships. Then, the X-ray irradiation can trace the top end of the catheter 31 by selectively irradiating the X-ray onto the X-ray focal position.

When the catheter 31 reaches the target position, the contrast medium M is injected from the other end of the catheter 31. The injected contrast medium M spreads over the peripheral blood vessels V. The injected contrast medium M spreads not only in a single blood vessel V, but also spreads over branches of the blood vessel V. The X-ray is irradiated from the X-ray focal position corresponding to a center position of the whole blood vessels where the contrast medium M is spreading over. At the center position of the whole blood vessels V, the immediately preceding image is subtracted from each of the images captured in chronological order, as is the case of the top end of the catheter 31. Here, there are differences that are dispersed in a plurality of positions. Therefore, a center of the dispersed positions is calculated to make it the X-ray focal position.

As described above, the X-ray is irradiated from the sequentially determined X-ray focal positions and X-ray radiographic images can be obtained based on moving images captured by tracing the contrast medium M that is spreading over the blood vessels V. If it is so configured that the X-ray focal positions, as target points selected after insertion of the catheter 31 or after injection of the contrast medium M, are continuously selected, the X-ray can be irradiated over an entirety of the inserted catheter 31 and the whole blood vessels V specified by the contrast medium M.

Figure 5:
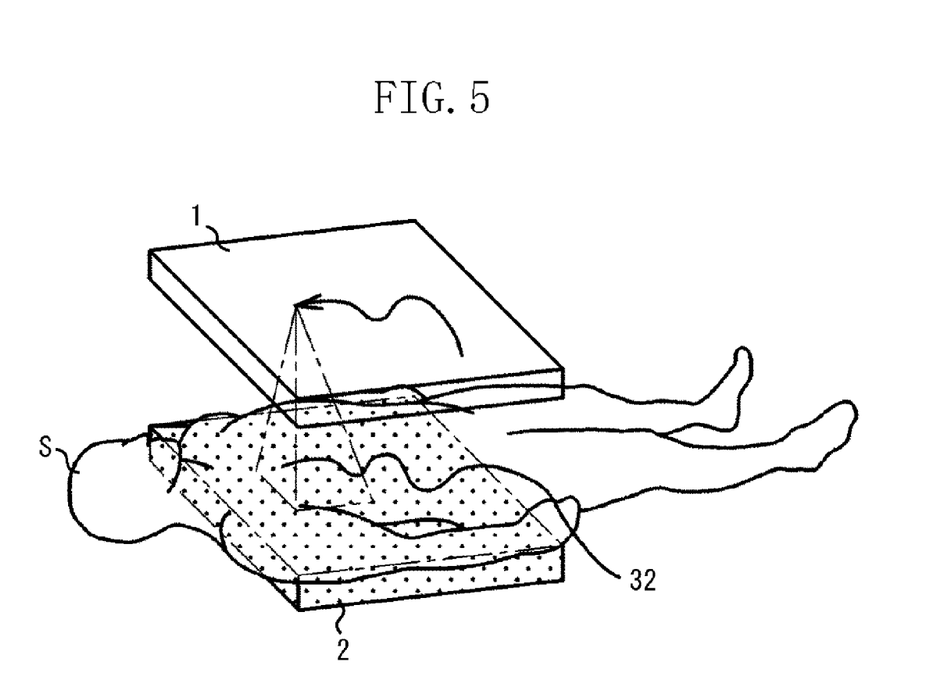
FIG. 5 illustrates how to capture images according to endoscope imaging.

FIG. 5 illustrates how to capture images by operating an endoscope according to a third exemplary embodiment. In the case of operating an endoscope 32, as in the case of using the catheter 31 according to the second exemplary embodiment, a top end of the endoscope 32 is traced and the X-ray is irradiated to the subject by varying the X-ray focal positions.

In the third exemplary embodiment, a technique of energy subtraction is used in capturing the X-ray moving images in addition to what is described in the first and second exemplary embodiments. In the energy subtraction, energy of X-ray to be irradiated is varied by changing a tube voltage, the energy-varied X-ray is irradiated twice, and an image is formed according to a difference between the irradiations. The energy subtraction utilizes a property that materials have different X-ray absorption ratios according to the difference of energy. Therefore, the energy subtraction can provide a better image than a normal image that is captured when the X-ray is irradiated only once.

With the above described method, the energy subtraction X-ray radioscopic imaging can be performed by switching a degree of energy for each X-ray irradiation, irradiating the X-ray twice, and calculating the difference thereof.

Figure 6:
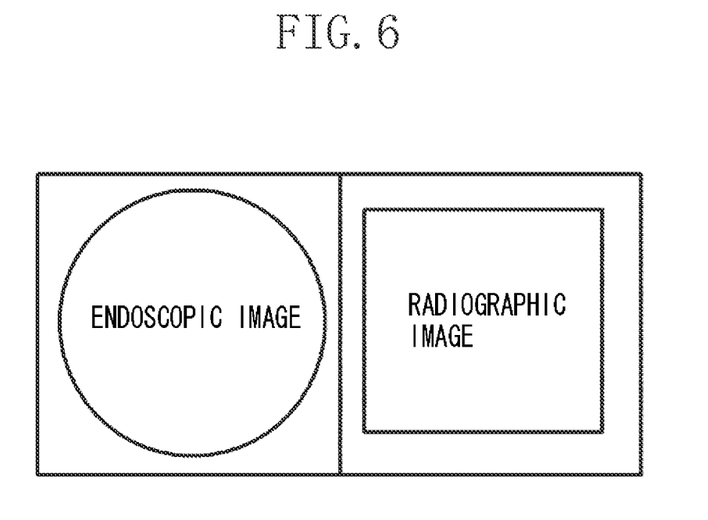
FIG. 6 illustrates a screen of a diagnostic diagnosis.

In the third exemplary embodiment, since the endoscope 32 is inserted into a body of the subject S, a positional relationship between a position of the body and an inside of the body can be effectively comprehended by displaying moving images of the endoscope on the diagnostic monitor 10 together with the X-ray moving images in a manner illustrated in FIG. 6.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-104300 filed on Apr. 14, 2008, which is hereby incorporated by reference herein in its entirety.

What is claimed is:

1. A control apparatus for controlling an X-ray source, the control apparatus comprising:
    a first acquisition unit configured to acquire an endoscopic image from an endoscope inserted in a subject;
    a second acquisition unit configured to acquire an X-ray image of the endoscope in the subject by detecting with an X-ray detector an X-ray emitted from the X-ray source;
    a determination unit configured to determine a position of the endoscope in the subject based on the X-ray image of the endoscope;
    a radiation control unit configured to control the X-ray source to emit an X-ray to capture a next X-ray image of the endoscope based on the determined position of the endoscope; and
    a display control unit configured to display on a display unit the endoscopic image acquired from the endoscope together with the captured next X-ray image.

2. The control apparatus of claim 1,
    wherein the control unit is configured to select an X-ray focal point from a plurality of X-ray focal points of the X-ray source, and
    wherein the control apparatus further comprises a storage unit configured to store a correspondence relationship between the X-ray image and the X-ray focal point as a table.

3. The control apparatus of claim 1, wherein the control unit is further configured to determine a top end of the endoscope as a target point of the subject based on a change between the X-ray image and the next x-ray image.

4. The control apparatus of claim 1, further comprising:
    an image processing unit configured to generate an energy subtraction image from the X-ray image and the next X-ray image,
    wherein irradiations for the X-ray image and the next X-ray image are different from each other in X-ray energy.

5. The control apparatus of claim 1, wherein the control unit is configured to acquire, based on a change between the X-ray image and the next x-ray image, a region where contrast medium is in the subject.

6. An X-ray imaging apparatus comprising:
    a control apparatus of claim 1; and
    a X-ray detector defining a 2-dimensional detection area configured to detect an X-ray to generate a X-ray image.

7. The X-ray imaging apparatus of claim 6, further comprising:
    a display unit configured to display the X-ray image and the endoscopic image.

8. The X-ray imaging apparatus of claim 6, further comprising a X-ray source having a plurality of X-ray focal points.

9. The X-ray imaging apparatus of claim 6, further comprising:
    an X-ray detector defining a 2-dimensional detection area and configured to detect an X-ray to generate a X-ray image;
    a X-ray source having a plurality of X-ray focal points;

a C-arm member coupled to the X-ray detector at one end and coupled to the X-ray source at another end, configured to rotate the X-ray detector and the X-ray source around the subject.

10. The X-ray imaging apparatus of claim 6, further comprising:
an endoscope having a shape insertable into the subject, configured to obtain an endoscopic image inside the subject.

11. The control apparatus of claim 1, wherein the display control unit is configured to display the acquired endoscopic image and the acquired X-ray image in which a top end of the endoscope that has captured the acquired endoscopic image is captured.

12. The control apparatus of claim 1, wherein the display control unit is configured to display the endoscopic image together with next X-ray image in which a top end of the endoscope is captured.

13. The control apparatus of claim 1, wherein the display control unit is configured to chronologically display the X-ray image and the next X-ray image so that a traced top end of the endoscope is captured.

14. The control apparatus of claim 12, further comprising:
an image processing unit configured to analyze the X-ray image and the next X-ray image in order to track the top end of the endoscope.

15. A method for controlling an X-ray source, the method comprising;
acquiring an endoscopic image from an endoscope inserted in a subject;
acquiring an X-ray image of the endoscope in the subject by detecting with an X-ray detector an X-ray emitted from the X-ray source;
determining a position of the endoscope in the subject based on the X-ray image;
controlling the X-ray source to emit an X-ray to capture a next X-ray image of the endoscope based on the determined position of the endoscope; and
controlling to display on a display unit the endoscopic image together with the next X-ray image.

16. A non-transitory computer-readable storage medium storing a computer-executable program including instructions to cause at least one computer to execute a process for controlling an X-ray source, the program comprising:
instructions for acquiring an endoscopic image from an endoscope inserted in a subject;
instructions for acquiring an X-ray image of the endoscope in the subject by detecting with an X-ray detector an X-ray emitted from the X-ray source;
instructions for determining a position of the endoscope in the subject based on the X-ray image;
instructions for controlling the X-ray source to emit an X-ray to capture a next X-ray image of the endoscope based on the determined position of the endoscope; and
instructions for controlling to display on a display unit the endoscopic image together with the next X-ray image.

* * * * *